United States Patent [19]
Heck

[11] Patent Number: 5,709,335
[45] Date of Patent: Jan. 20, 1998

[54] SURGICAL STAPLING INSTRUMENT AND METHOD THEREOF

[75] Inventor: Christopher Francis Heck, Palo Alto, Calif.

[73] Assignee: Heartport, Inc., Redwood City, Calif.

[21] Appl. No.: 550,285

[22] Filed: Oct. 31, 1995

Related U.S. Application Data

[63] Continuation of Ser. No. 261,167, Jun. 17, 1994, abandoned.

[51] Int. Cl.$^6$ ................................................. A61B 17/068
[52] U.S. Cl. ...................... 227/176.1; 227/19; 227/177.1
[58] Field of Search ............................. 227/175.1, 176.1, 227/178.1, 179.1, 180.1, 19

[56] References Cited

U.S. PATENT DOCUMENTS

| | | |
|---|---|---|
| 1,251,258 | 12/1917 | Magill . |
| 1,918,890 | 7/1933 | Macomb . |
| 2,434,030 | 1/1948 | Yeomans . |
| 2,638,901 | 5/1953 | Sugarbaker . |
| 2,707,783 | 5/1955 | Sullivan . |
| 3,040,748 | 6/1962 | Klein et al. . |
| 3,080,564 | 3/1963 | Strekopitov . |
| 3,193,165 | 7/1965 | Akhalaya . |
| 3,217,557 | 11/1965 | Martinot . |
| 3,252,643 | 5/1966 | Strekopytov . |
| 3,269,630 | 8/1966 | Fleischer . |
| 3,388,847 | 6/1968 | Kasulin . |
| 3,452,615 | 7/1969 | Gregory . |
| 3,494,533 | 2/1970 | Green et al. . |
| 3,552,626 | 1/1971 | Astafiev . |
| 3,589,589 | 6/1971 | Akopov . |
| 3,593,903 | 7/1971 | Astafiev . |
| 3,638,652 | 2/1972 | Kelley . |
| 3,692,224 | 9/1972 | Astafiev et al. . |
| 3,805,793 | 4/1974 | Wright . |
| 4,166,466 | 9/1979 | Jarvik . |

(List continued on next page.)

FOREIGN PATENT DOCUMENTS

| | | |
|---|---|---|
| 0 137 685 | 4/1985 | European Pat. Off. . |
| 7711347 | 10/1977 | Netherlands . |
| 99576 | 2/1983 | U.S.S.R. . |
| 109 7301 | 6/1984 | U.S.S.R. . |
| 2 038 692 | 7/1980 | United Kingdom . |
| 2108418 | 5/1983 | United Kingdom . |

OTHER PUBLICATIONS

Vogelfanger, et al., "A Concept of Automation in Vascular Surgery: A Preliminary Report on a mechanical instrument for Arterial Anastomosis"; *Canadian Journal of Surgery*; vol. 1; Apr. 1958; pp. 262–265.

*Primary Examiner*—Scott A. Smith
*Attorney, Agent, or Firm*—Jeffry J. Grainger; Jens E. Hoekendijk; Michael L. Louie

[57] ABSTRACT

A surgical stapling instrument for stapling a tubular tissue structure having at least one distal end to a luminal structure, such as a vascular lumen or another tubular tissue structure. The instrument comprises a rod having a circumference sufficient to pass within the tubular tissue structure, an anvil mounted on the rod, and a generally tubular staple cartridge for containing a plurality of staples. The anvil has an array of staple deforming mechanism thereon and is of a size sufficient to pass through a surgically formed opening in and to be accommodated within the luminal structure. The inner passage of the staple cartridge is sufficient to axially accommodate the tubular tissue structure between the rod and the inner surface of the staple cartridge, and sufficient to allow the staple cartridge to be moved axially along the rod. The staple delivery end of the staple cartridge is positioned toward the staple deforming mechanism of the anvil and has an outer dimension small enough so that the tubular tissue structure can be everted thereover. A clamping mechanism secures the everted portion of the tubular tissue structure and the luminal structure adjacent to the surgically formed opening between the staple cartridge and the anvil. A plurality of staples may then be ejected to pass through the everted portion of the tubular tissue structure and the luminal structure to engage the staple deforming mechanism to deform the staples and create a bond between the tubular tissue structure and the luminal structure.

43 Claims, 13 Drawing Sheets

U.S. PATENT DOCUMENTS

| | | |
|---|---|---|
| 4,304,236 | 12/1981 | Conta et al. . |
| 4,319,576 | 3/1982 | Rothfuss . |
| 4,325,376 | 4/1982 | Klieman et al. . |
| 4,350,160 | 9/1982 | Kolesov et al. . |
| 4,573,468 | 3/1986 | Conta et al. . |
| 4,576,167 | 3/1986 | Noiles . |
| 4,586,503 | 5/1986 | Kirsch et al. . |
| 4,603,693 | 8/1986 | Conta et al. . |
| 4,646,745 | 3/1987 | Noiles . |
| 4,703,887 | 11/1987 | Clanton et al. ............................ 227/19 |
| 4,917,090 | 4/1990 | Berggren et al. . |
| 4,917,091 | 4/1990 | Berggren et al. . |
| 4,957,499 | 9/1990 | Lipatov et al. . |
| 5,119,983 | 6/1992 | Green et al. . |
| 5,197,649 | 3/1993 | Bessler et al. ............................ 227/19 |
| 5,271,543 | 12/1993 | Grant et al. . |
| 5,292,053 | 3/1994 | Bilotti et al. ............................ 227/19 |
| 5,333,773 | 8/1994 | Main et al. . |
| 5,348,259 | 9/1994 | Blanco et al. ............................ 227/19 |

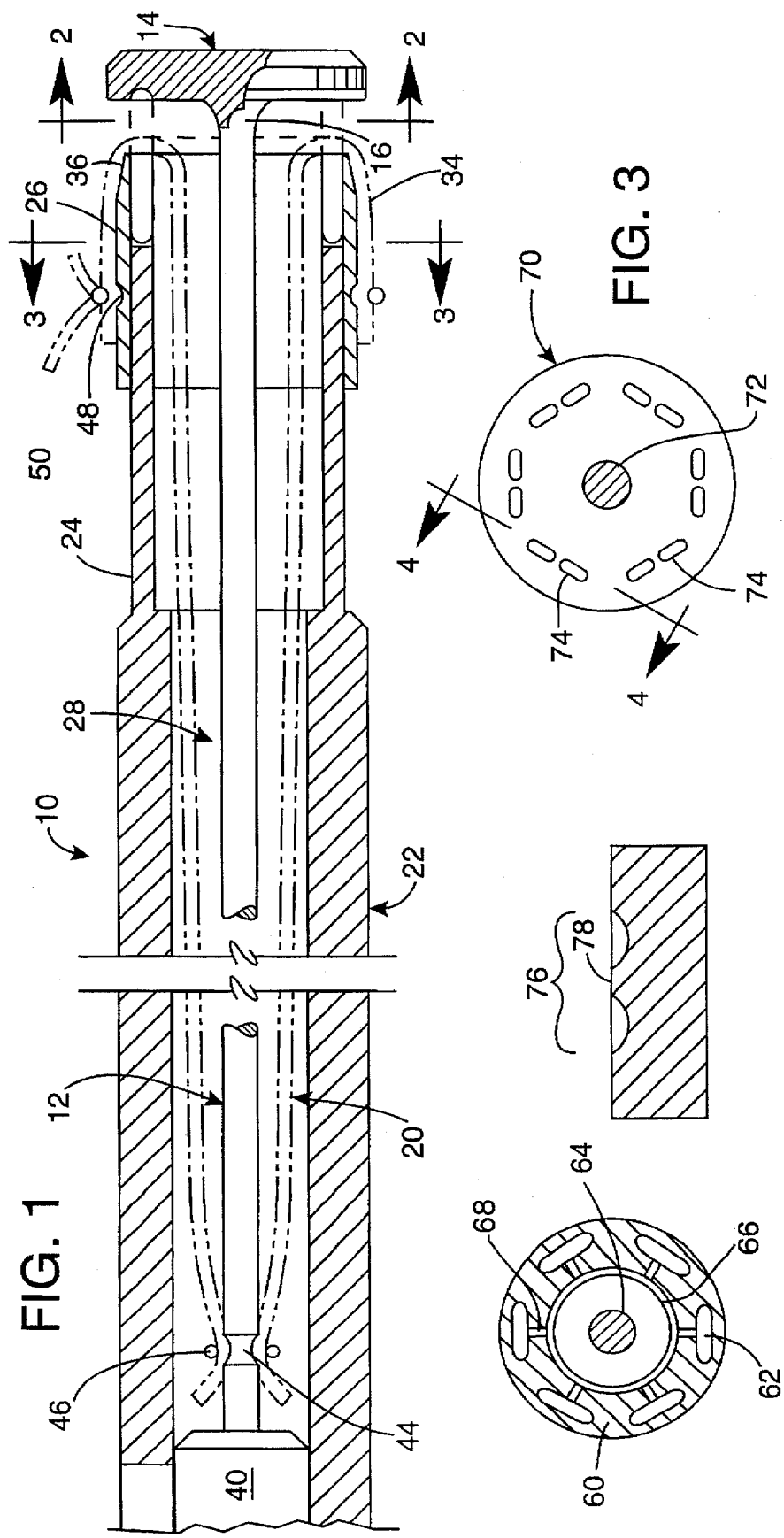

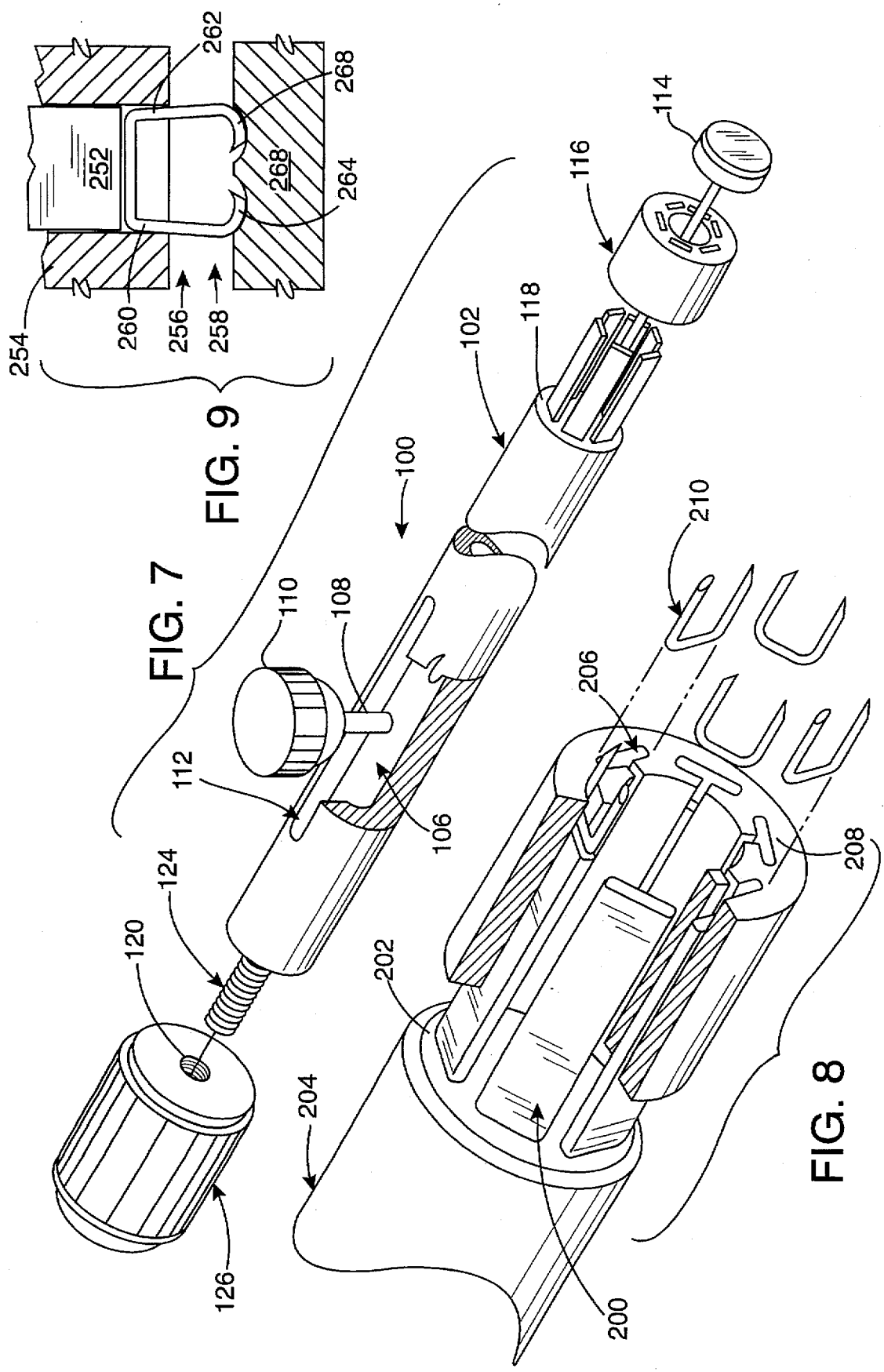

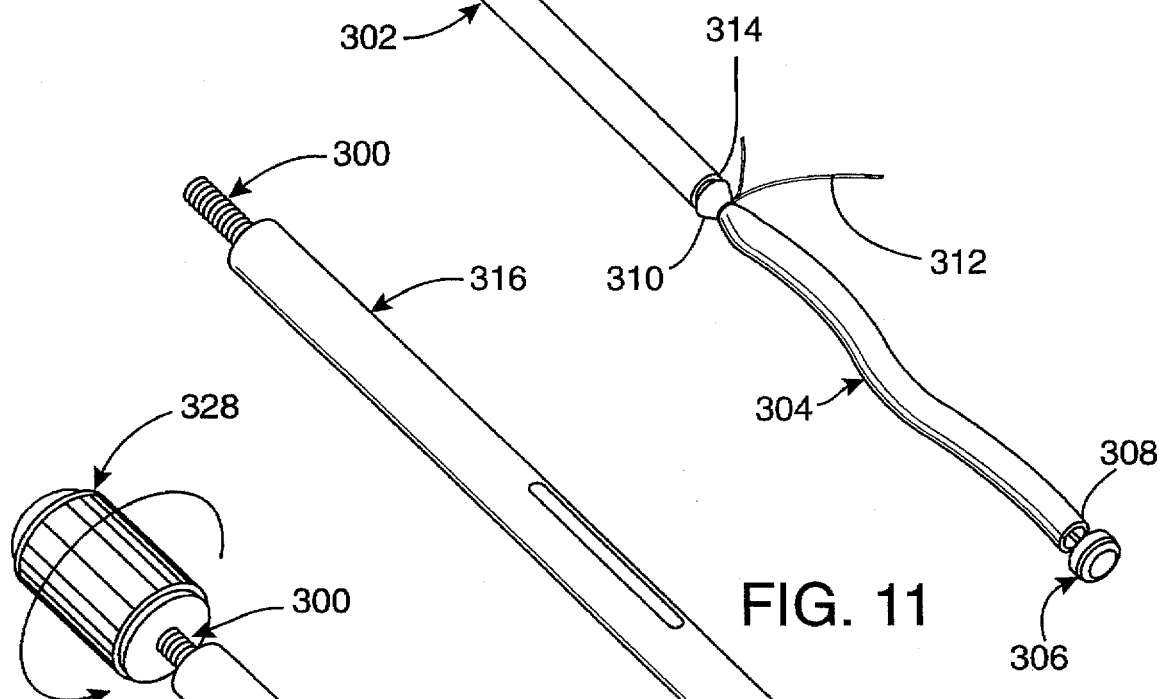
FIG. 10
FIG. 11
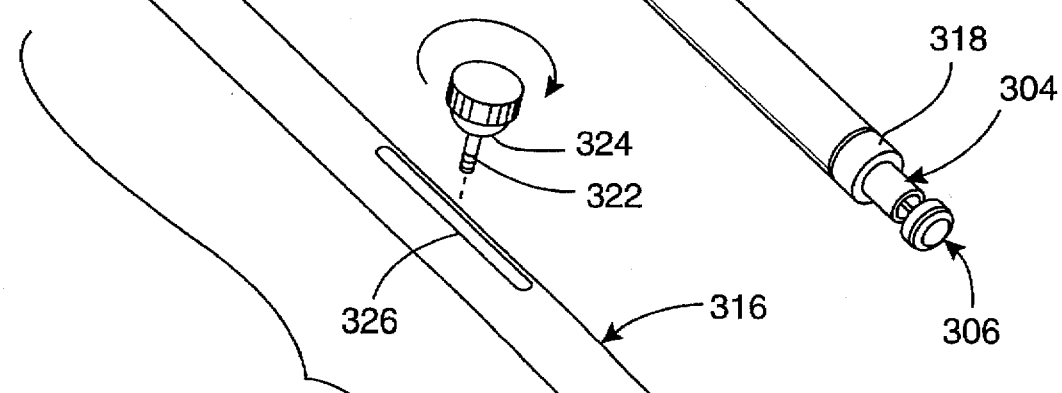
FIG. 12

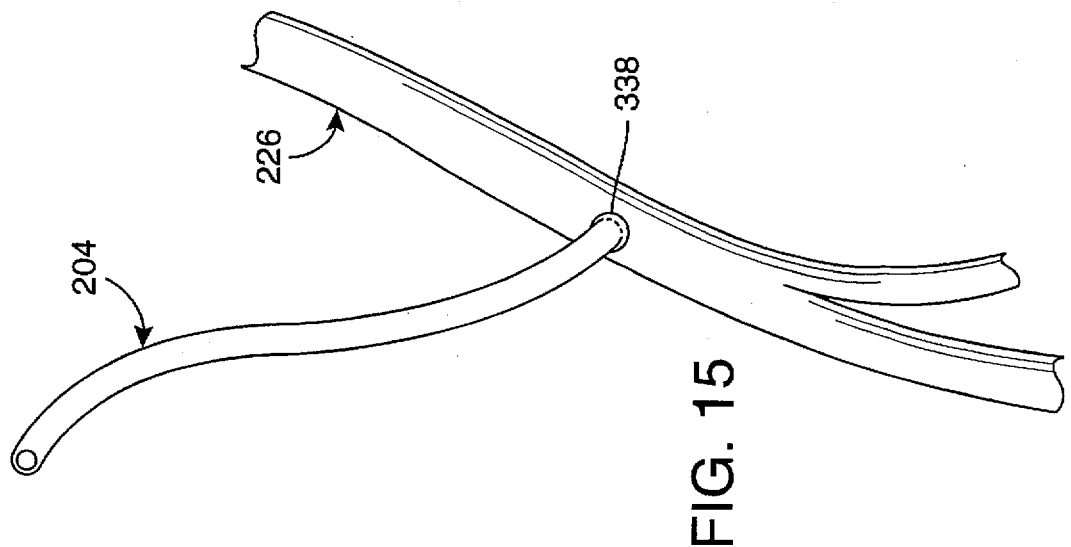
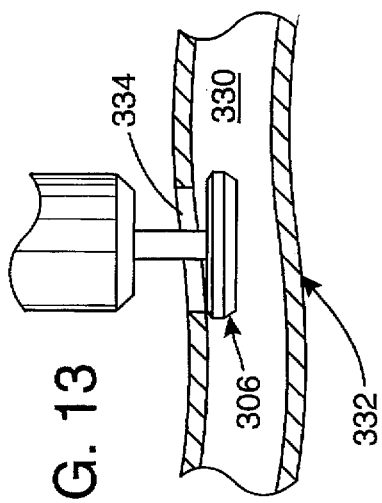
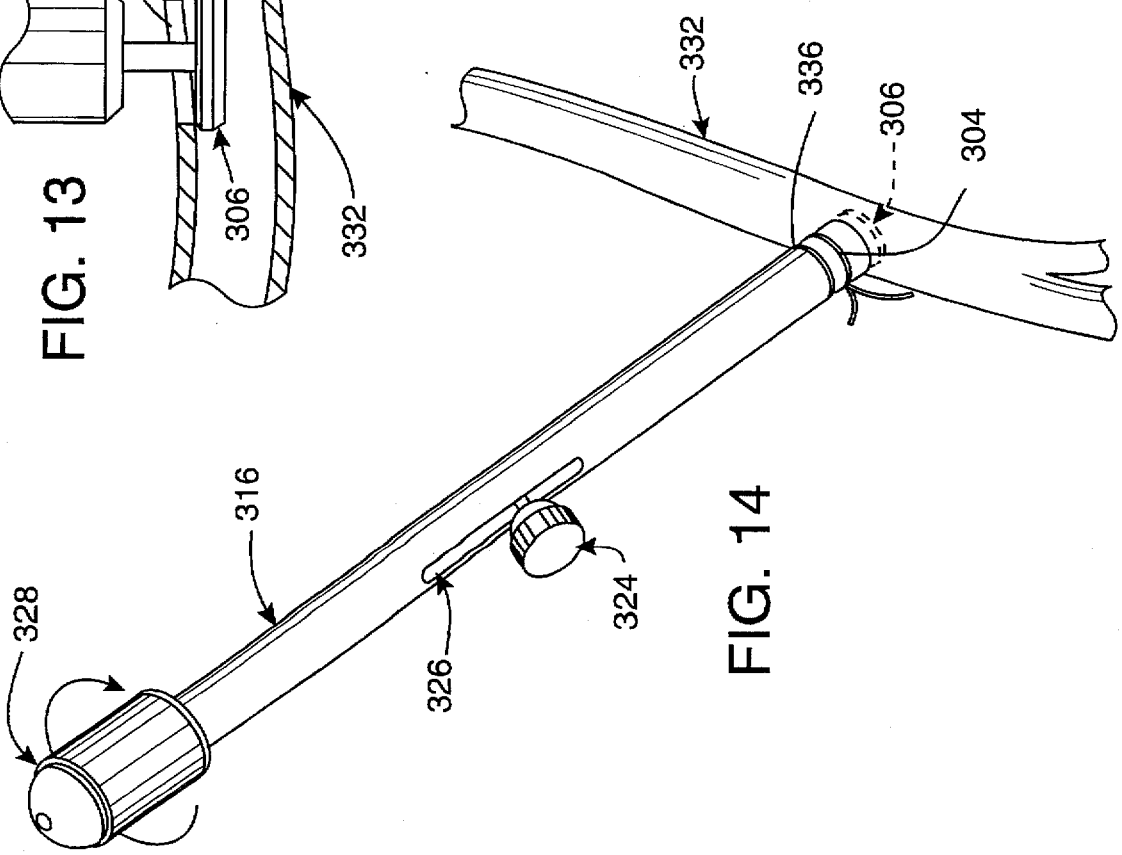
FIG. 13
FIG. 14
FIG. 15

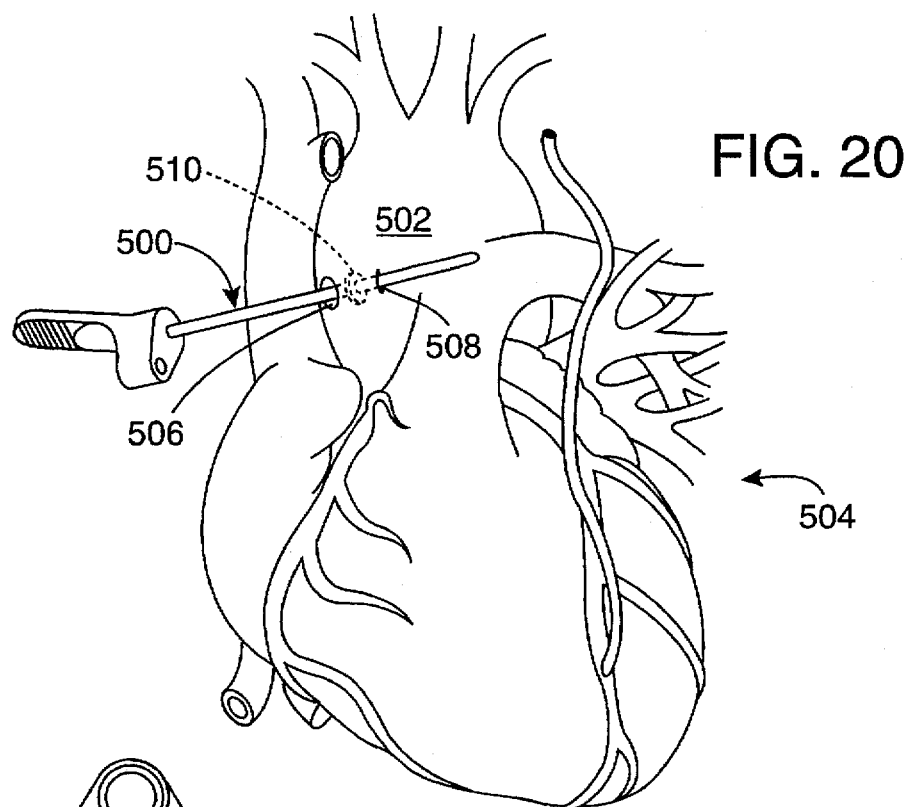
FIG. 20
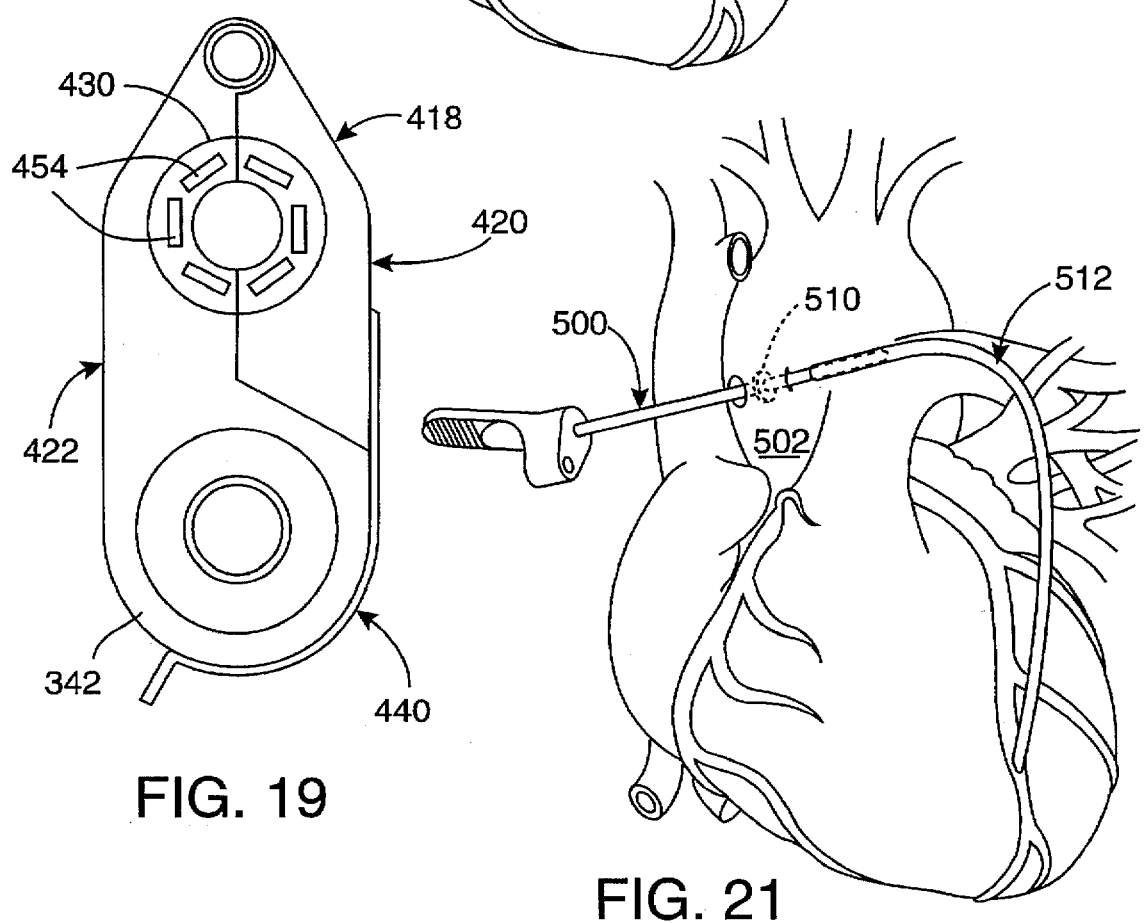
FIG. 19
FIG. 21

SURGICAL STAPLING INSTRUMENT AND METHOD THEREOF

This application is a continuation, of application Ser. No. 08/261,167 filed Jun. 17, 1994, now abandoned.

FIELD OF THE INVENTION

The invention relates generally to surgical stapling appliances and more particularly to an improved apparatus and method for the anastomotic surgical stapling of luminal organs, such as vascular lumens.

BACKGROUND OF THE INVENTION

Various instruments are known in the prior art for end-to-end and end-to-side anastomotic surgical stapling together of parts of the alimentary canal (i.e., esophagus, stomach, colon, etc.). These instruments employ staple cartridges, generally in the shape of a hollow cylinder, of different sizes to accommodate tubular organs of varying diameters. End-to-end and end-to-side anastomoses are achieved by means of at least one ring of surgical staples.

The traditional technique for surgical stapling anastomosis is to position the stapling cartridge within the tubular organ to be stapled. The cut end of the tubular organ is inverted (i.e., folded inwardly) over the annular end of the staple cartridge creating an inverting anastomosis upon stapling. An essential requirement of the inverting anastomotic technique is the incorporation of knives within the staple cartridge housing to trim excess tissue from the anastomotic connection.

The prior art anastomotic stapling instruments form generally circular anastomotic connections, and have been largely limited to alimentary organs. With respect to end-to-side vascular anastomosis, circular connections, rather than an elliptical connections, are sometimes disadvantageous as they are less physiologic or natural. This unnatural connection may create turbulence in the blood flow as it courses through the anastomosis, damaging the intima (i.e., inner wall) of the blood vessel and predisposing it to forming blood clots.

In the present state of the art, end-to-end and end-to-side anastomosis between blood vessels have typically been accomplished by hand-sewn suturing techniques. These techniques are time consuming, not as reliable as stapling, and subject to greater human error than stapling. Current stapling instruments used for alimentary canal are not suitable, however, for vascular anastomosis due to their large sizes and inability to provide non-circular and low turbulence anastomoses. A typical prior art instrument has a circumference of approximately 8 cm (3 in), far too thick to accommodate coronary arteries and veins, which have circumferences ranging from 0.50 to 1.0 cm and from 1.5 to 2.5 cm, respectively.

An additional drawback of prior stapling instruments is the inability to provide an everted (i.e., folded outwardly) anastomosis. An inverted vascular anastomosis would expose the cut ends of the blood vessels to the vessel lumen and could lead to the formation of blood clots. For this reason, hand-sewn everted anastomoses for vascular connections are preferable, despite time and reliability drawbacks.

Accordingly, it is a general object of the present invention to provide an improved instrument and method for vascular anastomosis.

It is also an object of the present invention to provide a surgical stapling instrument small enough to accommodate vascular lumens.

Another object of the present invention is to provide a surgical stapling instrument for everted anastomosis.

Another object of the present invention is to provide a method for surgical stapling that does not require the removal of excess tissue from the anastomotical connection.

Still another object of the present invention is to provide an instrument and method for vascular anastomosis that is less time-consuming and more reliable than the prior art.

SUMMARY OF THE INVENTION

The present invention provides a novel instrument and method for vascular anastomoses which overcomes the drawbacks of prior art designs and achieves the aforesaid advantages.

Very generally, the surgical stapling instrument of the present invention is for stapling a tubular tissue structure having at least one distal end to a luminal structure, such as a vascular lumen or another tubular tissue structure. The instrument comprises a rod having a circumference sufficient to pass within the tubular tissue structure, an anvil mounted on the rod, and a generally tubular staple cartridge for containing a plurality of staples. The anvil has an array of staple deforming means theron, and is of a size sufficient to pass through a surgically formed opening in and to be accommodated within the luminal structure. The inner passage of the staple cartridge is sufficient to axially accommodate the tubular tissue structure between the rod and the inner surface of the staple cartridge, and sufficient to allow the staple cartridge to be moved axially along the rod. The staple delivery end of the staple cartridge is positioned toward the staple deforming means of the anvil and has an outer dimension small enough so that the tubular tissue structure can be everted thereover. A clamping mechanism secures the everted portion of the tubular tissue structure and the luminal structure adjacent to the sugically formed opening between the staple cartridge and the anvil. A plurality of staples may then be ejected to pass through the everted portion of the tubular tissue structure and the luminal structure to engage the staple deforming means to deform the staples and create a bond between the tubular tissue structure and the luminal structure.

DETAILED DESCRIPTION OF THE DRAWINGS

FIG. 1 is a fragmentary side elevation view, in cross section, of one embodiment of the anastomosis device constructed in accordance with the present invention and illustrating an end of the tubular tissue structure evened over the device end.

FIG. 2 is a front elevation view, in cross-section, of the anastomosis device taken substantially along the plane of the line 3—3 in FIG. 1

FIG. 3 is a rear elevation view, in cross-section, of the anastomosis device taken substantially along the plane of the line 2—2 in FIG. 1

FIG. 4 is a side elevation view, in cross-section, of the anvil of the anastomosis device taken substantially along the plane of the line 4—4 in FIG. 3

FIG. 7 is an exploded top perspective view, partially cut-away, of the anastomosis device of FIG. 1.

FIG. 8 is an enlarged, exploded, top perspective view, partially cut-away, of a staple cartridge assembly of the anastomosis device of FIG. 1.

FIG. 9 is an enlarged, side elevation view, in cross-section, of the anvil and staple cartridge assembly of the anastomosis device of FIG. 1 illustrating the deformation of a staple.

FIGS. 10–12 is a sequence of top perspective views illustrating the loading of a tubular tissue structure in the anastomosis device of FIG. 1

FIG. 13 is an enlarged, side elevation view, in partial cross-section, showing the positioning of the anvil of the anastomosis device through a luminal structure.

FIG. 14 is a reduced top perspective view of the anastomosis device of FIG. 1 mounted to the luminal structure.

FIG. 15 is a reduced top perspective view of the tubular tissue structure anastomotized to the luminal structure using the anastomosis device of FIG. 1.

FIG. 19 is an end view of the staple cartridge assembly of FIG. 18.

FIGS. 20–22, 24, 25, 27 and 28 is sequence of top perspective views illustrating the application of the alternative embodiment anastomosis device of FIG. 17 for proximal anastomosis of the grafted tubular tissue structure to the ascending aorta.

DETAILED DESCRIPTION OF THE INVENTION

Figure 5:
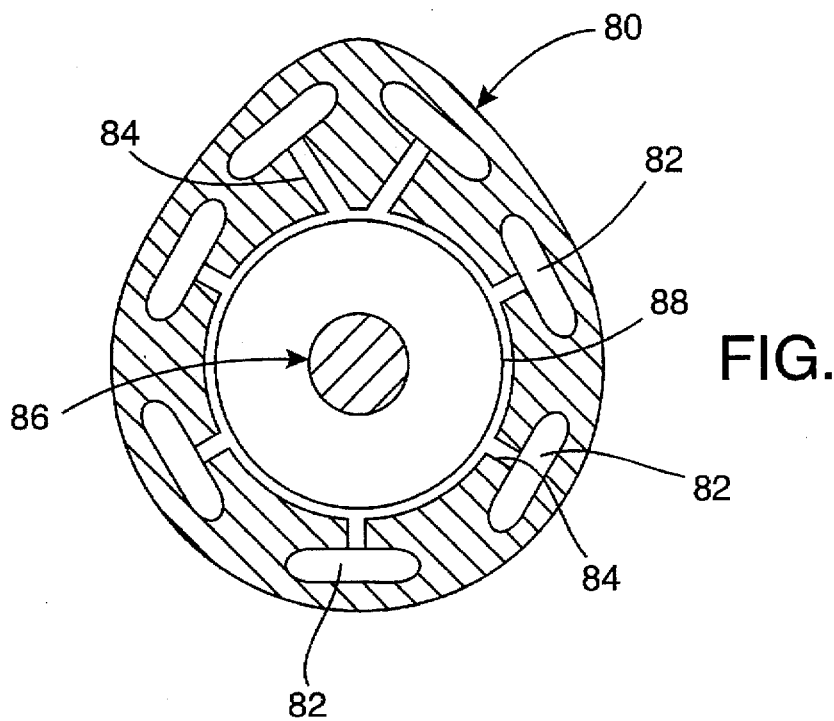
FIG. 5 is a front elevation view, in cross-section, of an alternative embodiment of FIG. 3 illustrating a tear drop-shaped configuration.

Referring to FIGS. 1–7, there is shown a structural embodiment of the present invention which is best suited for anastomotic stapling of a tubular vessel having two distal or untethered ends. As will be evidenced by the detailed description below, this embodiment, i.e., distal stapler, is ideal for use during cardiopulmonary bypass surgery for making the primary anastomotic connection of a bypass vein to a coronary artery or to the aorta.

Referring now to FIG. 1, a portion 10 of the wholly configured distal stapler of the present invention, as shown in FIG. 7, comprises an elongated central rod 12 with anvil 14 mounted at its distal end 16. Anvil 14 is in the form of a circular, elliptical or tear drop-shaped disk and is mounted, by suitable means such as welding, to the end of central rod 12 transversely thereof and at the center of the anvil. The edges of anvil 14 are beveled or otherwise generally rounded to enable anvil 14 to slip easily through incisions in vascular walls—much like a button through a button hole.

The central rod 12 has a circumference sufficient to permit the rod to axially extend through a tubular vessel, indicated in phantom at 20, to be stapled. Central rod 12 also axially extends within tubular housing 22, driver pins 24 and staple cartridge 26, together forming a contiguous shaft 28 having an inner circumference sufficient to accommodate tubular vessel 20 sandwiched between them and central rod 12. Staple cartridge 26 has an outer circumference sufficient to accommodate everted end 34 of tubular vessel 20. Lip 36 of cartridge 26 is tapered to facilitate eversion of tubular vessel 20. Anvil 14 has circumference of a size equivalent to the outer circumference of staple cartridge 16.

Circumferences of vascular vessels range from 0.50 to 1.0 cm for coronary arteries and from 1.5 to 2.5 cm for veins. Accordingly, all circumferences, discussed above, of stapler 10 are of a size to optimally coaxially accommodate the vein to be stapled.

The end of central rod 12 opposite anvil 14 is centrally mounted, preferably welded, on a cylindrical base 40 which extends coaxially within tubular housing 22 (as shown in FIG. 7 by reference number 106) and has a circumference sufficient to be slidable within tubular housing 22. The accommodated tubular vessel 20 extends along central rod 12 to cylindrical base 40. Provided on the surface of central rod 12 proximal to base 40 is circumferential groove 44 for facilitating the securing of tubular vessel 20 to rod 12 by means of string 46. Similarly, circumferential groove 48 and string 50 are provided to secure everted end 34 of vessel 20 to staple cartridge 26. An alternative embodiment of staple cartridge 26 for securing an everted vein comprises tiny hooks around the circumference at end 36 of the cartridge. Other suitable means for accomplishing the securing function may be used as well.

Referring now to FIG. 2, there is shown a cross-sectional view of stapler 10 of the present invention in the direction of arrows 2—2 of FIG. 1. Here, the staple delivery end 60 of a circular staple cartridge is illustrated encasing a circular array of staple delivery means or staple shafts 62. The present invention is not limited to a single staple shaft array, however. It is commonly known in the art to employ a plurality of concentric arrays or rows of staple shafts for anastomotic procedures. Extending from staple shaft array 62, is an array of narrow channels 68, each narrow channel corresponding to each staple shaft. Channel array 68 is used solely for manufacturing purposes and is not a necessary element of the invention. Central rod 64 and its base 66 are axially and centrally located within the cylindrical staple cartridge 60.

FIG. 3 shows the underside view of anvil 70 in the direction of arrows 3—3 of FIG. 1. The anvil 70 has an array 74 of means for deforming staples. Central rod attachment 72 is centrally located on anvil 70 which provides an array of staple deforming means 74, comprised here of an array of recess pairs, for bending staples projected from corresponding array of staple shafts 62 of the staple cartridge of FIG. 2.

Depicted in FIG. 4 is a cross-sectional view of anvil 70 in the direction of arrows 4—4 of FIG. 3. Each recess pair 76 is curved to bend staple legs radially inward. The projected staples can be made to bend radially inward or radially outward depending on the spacing 78 between the recess of each paired recess 76. Alternatively, each recess can be positioned orthogonal to its present position to bend the staple legs at right angles to their axis of projection.

Although the present invention is primarily described and depicted as forming staple bonds that are circular and as having component circumferences that are circular, other embodiments are realized for forming staple bonds having elliptical, tear drop or other generally oval circumferences. Accordingly, the anvil and associated staple recess array, and the cartridge housing and associated staple shaft array of these alternative stapler embodiments have circumferences in the shape of the desired staple bond. For example, FIGS. 5 and 6 illustrate an anvil and staple cartridge, respectively, having tear-drop shaped circumferences.

FIG. 5 shows a cross-sectional view of a tear-drop shaped staple cartridge. The staple delivery end 80 of the staple cartridge is llustrated encasing a tear drop array of staple delivery means or staple shafts 82. Extending from staple shaft array 82, is an array of narrow channels 84, each narrow channel corresponding to each staple shaft. Channel array 84 is used solely for manufacturing purposes and is not a necessary element of the invention. Central rod 86 and its base 88 are coaxially and centrally located within the cylindrical portion of dear drop staple cartridge 80.

Figure 6:
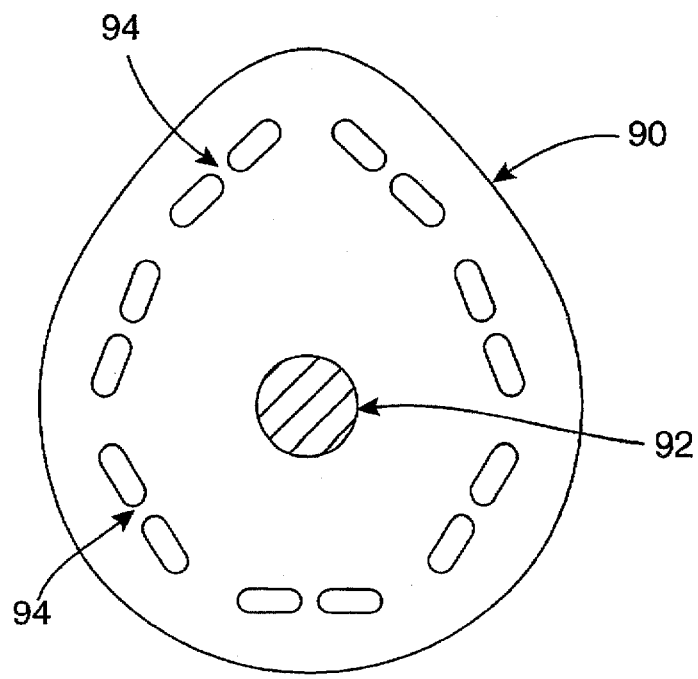
FIG. 6 is a rear elevation view, in cross-section, of the anvil of the alternative embodiment of FIG. 5 taken substantially along the plane of the line 2—2 in FIG. 1

FIG. 6 shows the underside view of a tear drop shaped anvil 90. Central rod attachment 92 is centrally located on the circular portion of anvil 90 which provides an array of staple deforming means comprised of recess pairs 94 for bending staples projected from corresponding array of staple shafts 82 of the staple cartridge of FIG. 5.

Referring now to FIG. 7, there is shown stapler 100 of the same embodiment depicted in FIGS. 1–4. A tubular housing 102 coaxially contains central rod 104 and rod base 106, the end of central rod 104 opposite that of anvil 114 being suitably mounted, such as by welding, to rod base 106 (connection not shown). Threadedly mounted to and extending perpendicular from rod base 106 is a short stem 108, positioned at approximately half the length of base 106. The top of stem 108 has cylindrical knob 110 transversely mounted. Stem 108 is moveable within narrow channel 112, cut within housing 102 and running parallel to the axis travelled by central rod 104 and rod base 106. Channel 112 limits the rotational movement of stem 108 and thereby maintains a proper radial orientation between anvil 114 and staple cartridge 116 during reciprocation.

Weldedly mounted to and protruding perpendicularly from cylindrical face 118 of housing 102 and paralleling rod 104 is cylindrical array of staple driver pins 120, all drivers pins being identical and each having the form of a solid parallelogram. Staple cartridge 116 encases, from end to end, cylindrical array of hollow staple shafts 122 which holds a plurality of preloaded staples (not pictured). All shafts 122 are identical and each has height and width dimensions such that a corresponding staple driver pin 120 is slidable therein.

In order to have an optimally functioning stapler, it is necessary to maintain a clean and clear passageway for central rod 104, base 106 and staple shafts 122. Accordingly, one embodiment of the present invention comprises a disposable cartridge which is disposed of and replaced after one anastomotic stapling. Another embodiment provides a slidable sleeve around the driver pin array to prevent blood and tissue from getting caught therein.

For anastomosis to be successful, it is imperative not to injure the living tissue being stapled by overcompressing it between anvil 114 and staple cartridge 116 or by a staple bond that is exceedingly tight. Accordingly, overcompression of the tissue is prevented in the present invention by limiting the length of driver pins 120. Other embodiments are known in the prior art for accomplishing this objective. For example, U.S. Pat. No. 4,573,468 employs mutually coacting stops located on the inner surface of a tubular housing and on the surface of a coaxial rod to provide variable degrees of engagement between tissues to be stapled so as to ensure against overcompression of the tissue. A spring-loaded engagement between the rod and tubular housing is also applicable for the present invention. Other means suitable for this purpose will be aparent to those having ordinary skill in the art.

Finally, FIG. 7 illustrates threaded end 124 of rod base 106 which extends beyond the length of housing 102 to threadedly engage with cylindrical nut 126 which has internally threaded throughbore 128 extending the full length of cylindrical nut 126 to allow end 124 to exit therethrough.

FIGS. 8 and 9 illustrate the mechanical interaction between the staple driver, staple cartridge and anvil upon engagement. FIG. 8 illustrates staple driver array 200 mounted on face 202 of tubular housing 204 slidably engaged within staple shaft array 206 of staple cartridge 208. Staple array 210 is projected from staple cartridge 208 and through the tissues to be stapled (not shown). FIG. 9 shows a close-up of a staple being driven by driver pin 252 and projecting through cartridge 254 through tissues 256 and 258. The legs 260 and 262 of staple 250 then engage with and bend along the curved recesses 264 and 266, respectively, of anvil 268 to form a bond between tissues 256 and 258.

Referring now to FIGS. 10–16, with like numbers referring to like elements, there is illustrated the steps of the anastomotic procedure using the structural embodiment described above. Now referring to FIG. 10 specifically, the anvil-headed end of rod base 302 is inserted into transected vein 304 having a length in the range of 10–18 cm (4–7 inches). End 308 (the end to be stapled) of vein 304 is positioned proximate to anvil 306. Opposing end 310 of vein 304 is tied with string 312 to central rod 314 at a circumferential depression (not shown) proximate to base 302.

FIG. 11 shows the step of inserting central rod 314 with attached vein 304 into staple cartridge 318 and tubular housing 316 such that staple cartridge 318 is proximate to anvil 306. FIG. 12 illustrates the next several steps of the method of the present invention which can be performed in any order. The end of vein 304 is everted over staple cartridge 318 and tied with string 320 securing it to staple cartridge 318 (covered by vein 304). Threaded stem 322 of cylindrical knob 324 is threadedly engaged with a threaded bore (not shown) base 302, the bore being aligned with narrow channel 326. Cylindrical nut 328 is threadedly engaged with the threaded end 300. As indicated in FIG. 13, anvil 306 is positioned within lumen 330 of vascular artery 332 via incision 334. A cross-section of a portion of vein 304 is shown everted over the staple delivery end of staple cartridge 318.

In FIG. 14, central rod 314 (not visible) and rod base 302 (not visible) are optimally coaxially positioned within tubular housing 316 by means of sliding knob 324 along channel 326 toward vascular artery 332. Nut 328 is rotated in a clockwise direction to engage it with tubular housing 316 causing rod base 302 to become rigidly interconnected with nut 328. As the clockwise turning continues, rod base 302 is drawn through the bore in nut 328, bringing the staple cartridge 336 and anvil 306 within artery 332 together. An embodiment employing mutually coacting stops (not shown) would, at this point, be at the first coacting position or the "loaded" position. The clockwise motion is continued so that everted vein 304 engages with the wall of artery 332 and until the staple drivers (not visible) are actuated, driving the staples (not visible) through the tissues to create a bond 338 (FIG. 15). If mutually coacting stops are employed, the configuration would be in the "firing" position.

Figure 16:
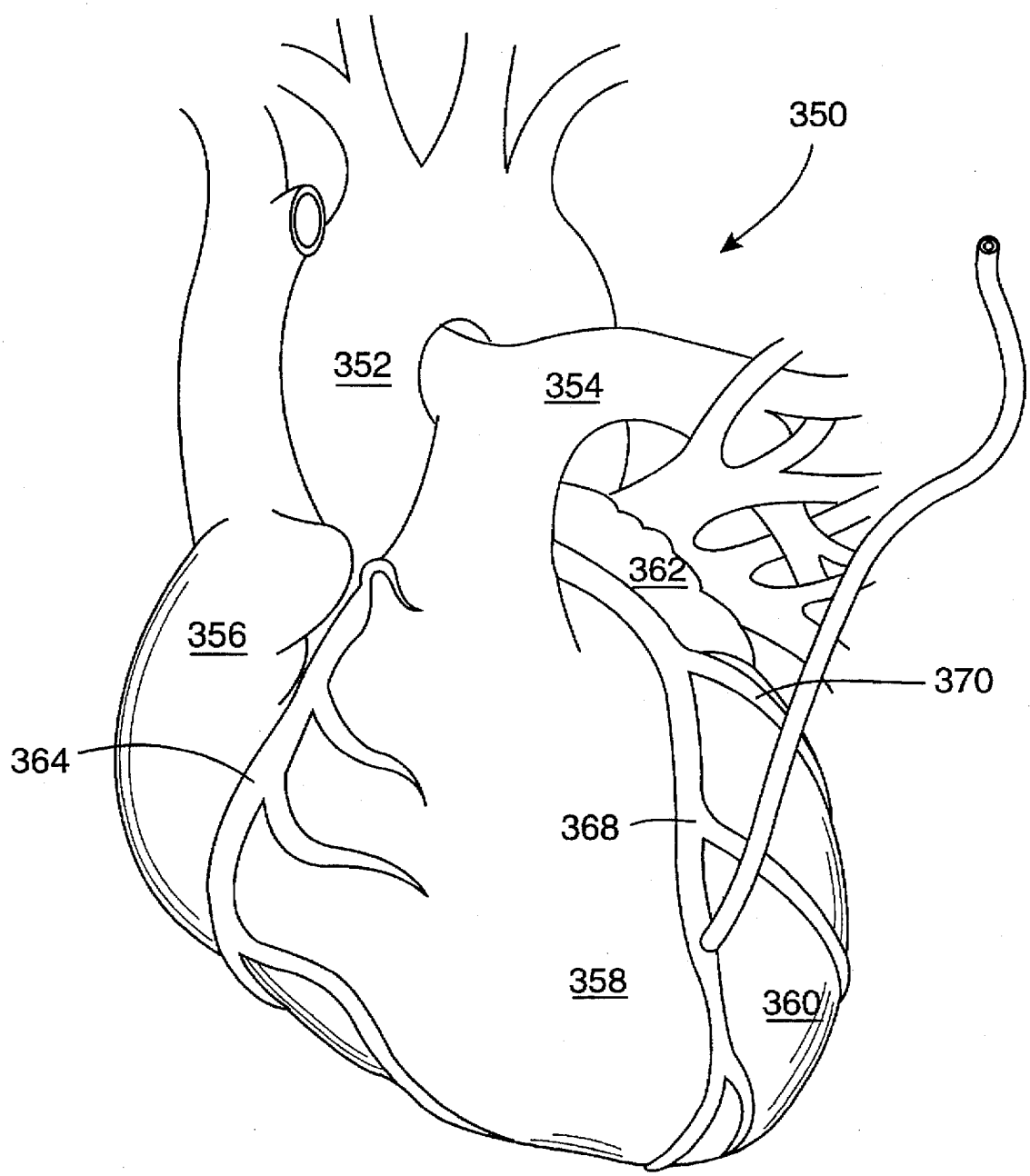
FIG. 16 is a front elevation view of a grafted tubular tissue structure anastomotized to a coronary artery of the heart through the anastomosis device of FIG. 1.

Finally, FIG. 16 illustrates heart 350 having aorta 352, pulmonary artery 354, right atrium 356, right ventricle 358, left ventricle 360, left atrial appendage 362, right coronary artery 364, left anterior descending artery 368, and diagonal artery 370. Here, vein 304 has been anastomotically stapled to left anterior descending artery 368.

To complete the anastomotic procedure of the bypass vein 304, the unstapled end of the anastomotized vein 304 must now be connected to aorta 352. However, another structural embodiment of the present invention, referred to as the "proximal" stapler, is needed since the embodiment described above, i.e., the "distal" stapler, requires the vein to have two distal or untethered ends. Accordingly, FIGS. 17–28 describe a structure and method thereof for a second embodiment of the present invention which is suited for the anastomotic stapling of a tubular vessel having only one distal end, the other end having already been anastomotically stapled.

Figure 17:
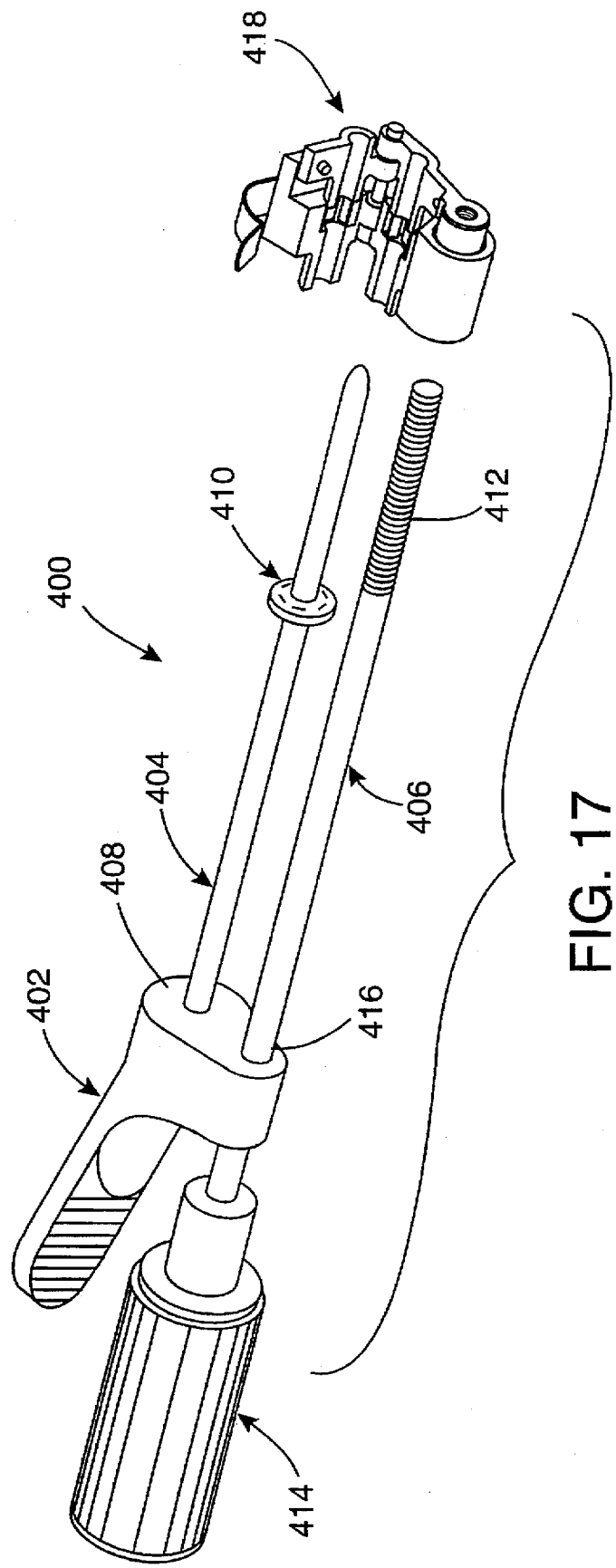
FIG. 17 is an exploded top perspective view of an alternative embodiment of the anastomosis device of the present invention.
Figure 18:
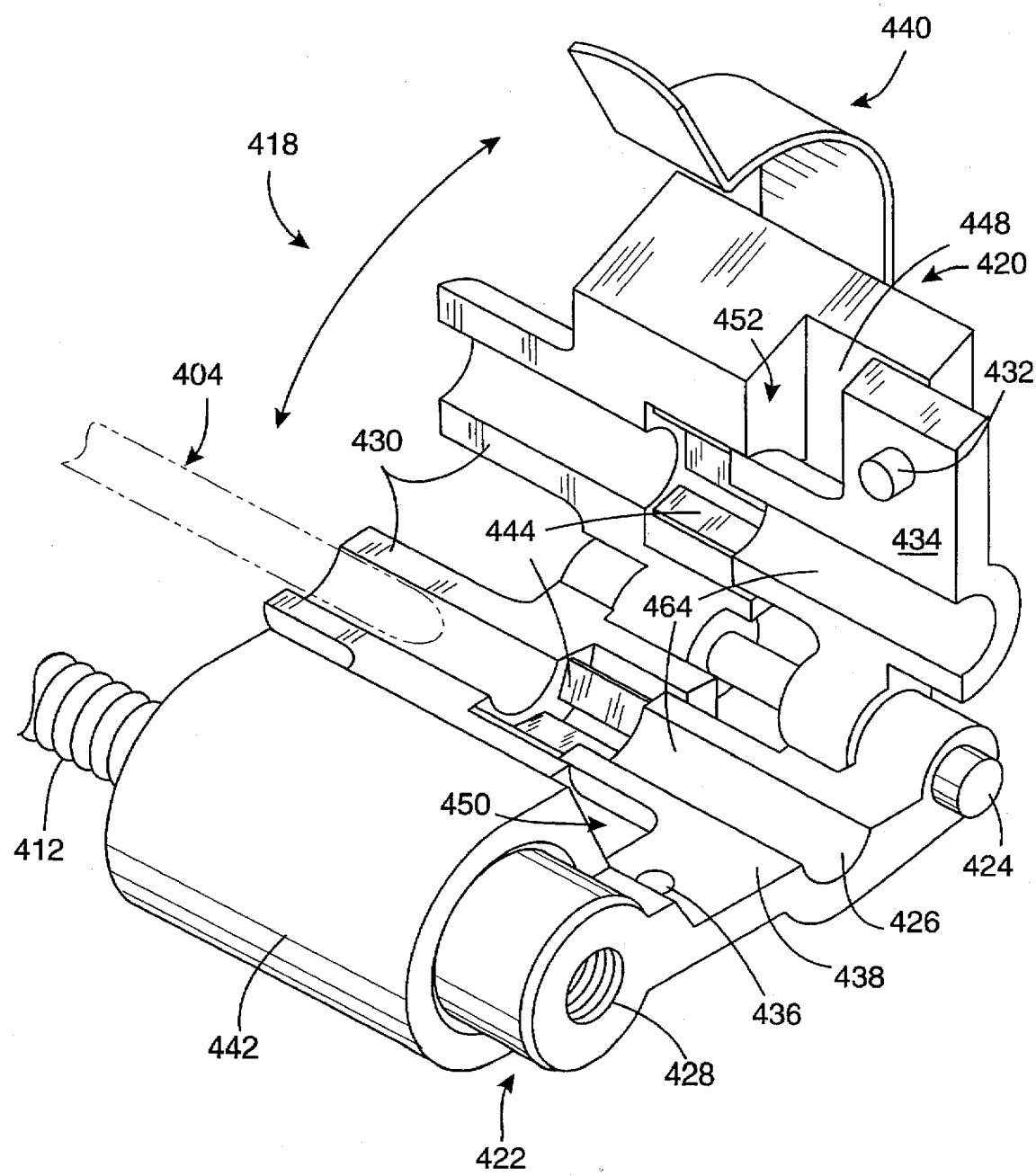
FIG. 18 is a fragmentary, enlarged top perspective view of a staple cartridge assembly of the alternative embodiment anastomosis device of FIG. 17.

Referring now to FIGS. 17–19, with like numbers referencing like elements, there is shown anastomotic stapler 400 having handle 402 with elongated vessel rod 404 and elongated driver rod 406 mounted perpendicularly to handle face 408 and parallel to each other, both being of approximately the same length. Vessel rod 404 has a centrally mounted generally circular anvil 410. Vessel rod 404 has a circumference sufficient to coaxially accommodate a tubular vessel (not shown) to be stapled to the aorta. Driver rod 406, having threaded end 412 and handle 414, extends through bore 416 of handle 402.

Stapler 400 also comprises staple cartridge 418, enlarged in FIG. 18 for purposes of describing its detail. Referring then to FIG. 18, there is shown the staple cartridge of FIG. 17 in its open position having top and bottom units 420 and 422, respectively. Units 420 and 422 are engaged at one side by hinge 424 which allows cartridge 418 to be opened and closed. Staple cartridge 418 has two parallel bores 426 and 428 with inner circumferences sufficient to coaxially accommodate vessel rod 404 with a coaxially accommodated vein (not shown) and driver rod 406, respectively. Staple delivery end 430 extends from staple cartridge 418 along the axis of bore 426 to accommodate the everted end of a vein to be stapled. Bore 428 is internally threaded to be threadedly engagable with driver rod end 412.

For a proper fit between units 420 and 422, a detent-recess pair is provided having detent 432 extending from inner surface 434 of top unit 420 which mates with recess 436 within inner surface 438 of bottom unit 422. To secure closing, a curved clip 440 is provided to fit around cylindrical casing 442 of bore 428.

When in a closed position, staple cartridge 418 has cylindrical staple delivery means or staple shaft array (not shown) encased in staple delivery end 430 which mates with cylindrical driver pin array 444 mounted on driver 446. Both the hollow shafts and the solid driver pins have height and width measurements that allow them to be slidably engageable with each other. Driver 446 is slidable along surface 448 of top unit 420 and surface 450 of bottom unit 422 to the point of engagement with shoulder 452 of top unit 420 upon which driver pin array 444 becomes engaged within the staple shaft array, projecting preloaded staples from the end of staple delivery end 430. Shoulder 452 limits the engagement of driver pin array 444 so that the tissue being stapled is not overcompressed. Modifications of the this embodiment can employ mutually coacting stops or spring-loaded type configurations between the driver and staple cartridge to prevent against overcompression of the tissue.

FIG. 19 shows a front view of staple cartridge 418 in its closed position with top unit 420 engaged with bottom unit 422. Clip 440 securely fits around cylindrical casing 442. Staple deforming end or staple shaft array 454 is shown on the face of staple delivery end 430.

FIGS. 20–28, with like numbers referencing like elements, depict the various steps of the anastomotic procedure using the structural embodiment in FIGS. 17–19 described above. Referring now to FIG. 20, vessel rod 500 is inserted through aorta 502 of heart 504 via incisions 506 and 508 on opposing walls of aorta 502 such that anvil 510 is centrally positioned within aorta 502.

Figure 22:
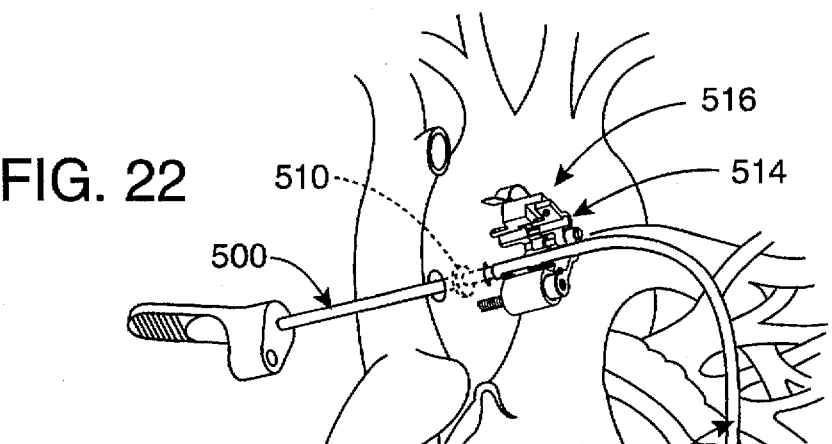
Figure 23:
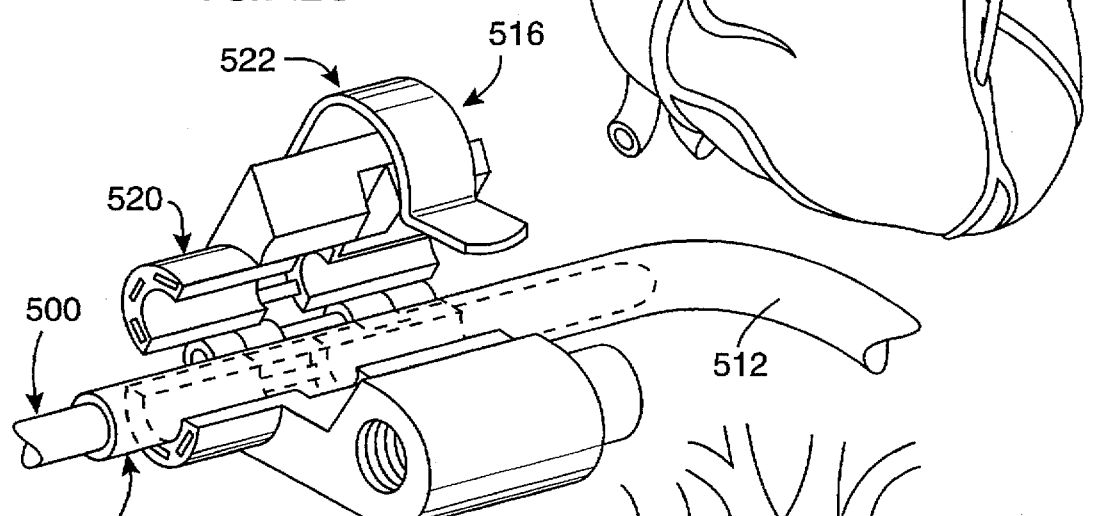
FIGS. 23 and 26 is a sequence of fragmentary, top perspective views illustrating the loading of a tubular tissue structure in the alternative embodiment anastomosis device of FIG. 17.
Figure 24:
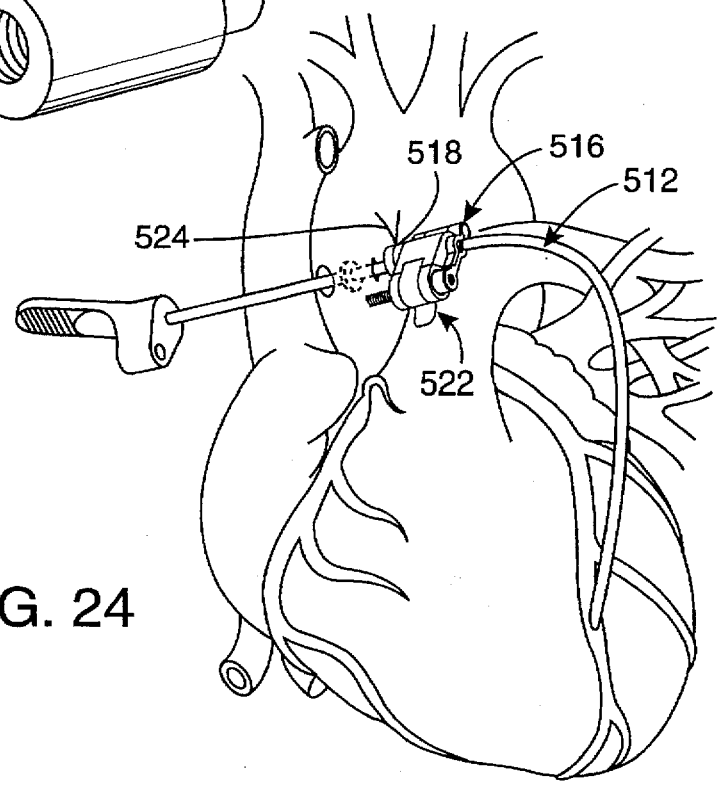

In FIG. 21, the end of vessel rod 500 is then inserted into the distal end of vein 512 with anvil 510 still centrally positioned within aorta 502. Next, as shown in FIG. 22, vessel rod 500 with accommodated vein 512 is positioned within the corresponding bore 514 in open staple cartridge 516. Rod 500 and vein 512 should be positioned such that a sufficient length of distal end 518 of vein 512 extends beyond the end of cartridge 516 such that distal end 518 can be everted over cylindrical sleeve 520 of cartridge 516 (See FIG. 23). Once vein 512 has been optimally positioned, staple cartridge 516 is clamped around it and secured with clip 522, illustrated in FIG. 24. Now, distal end 518 of vein 512 is everted over sleeve 520 and is securely tied with string 524.

Figure 25:
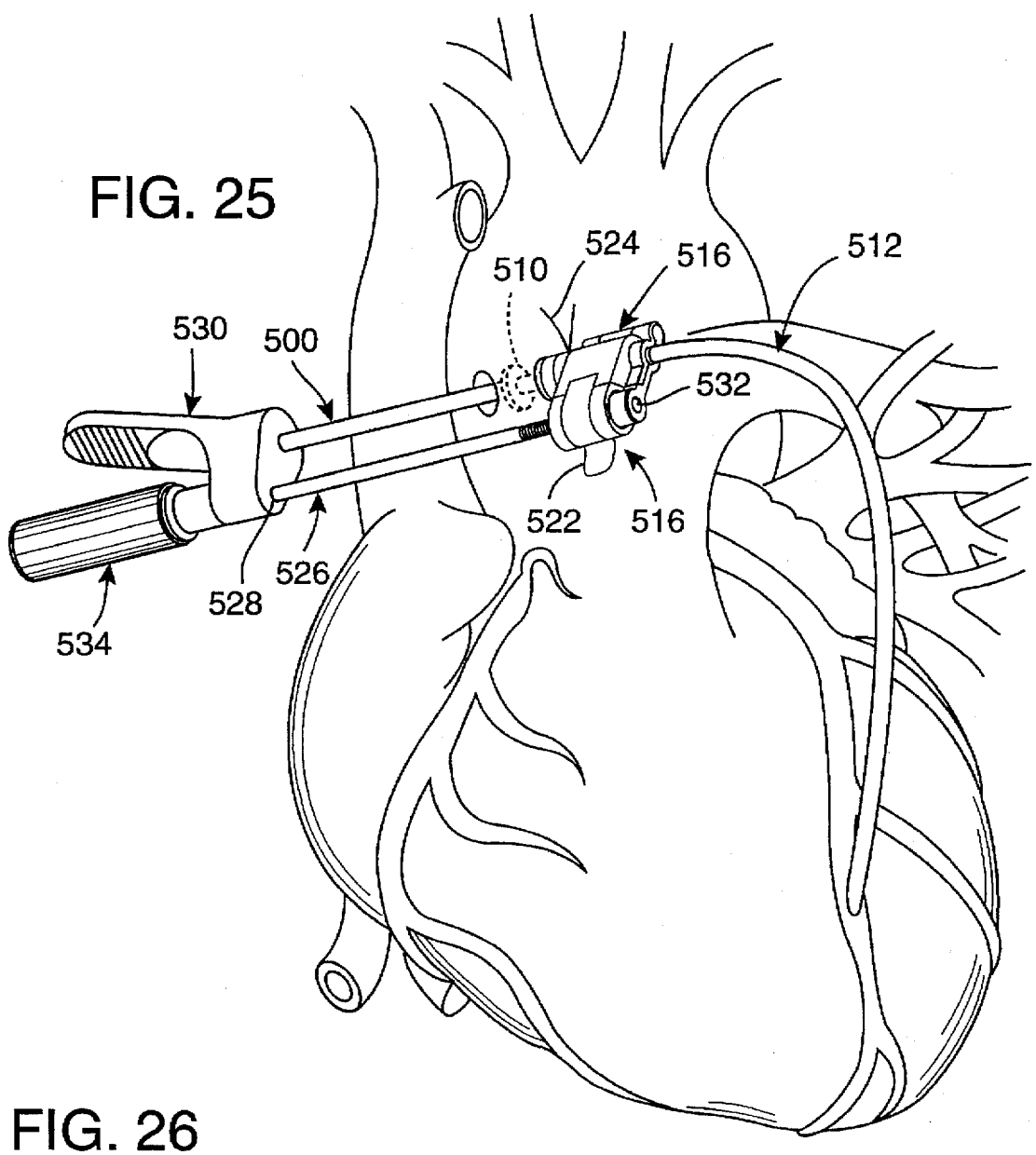
Figure 26:
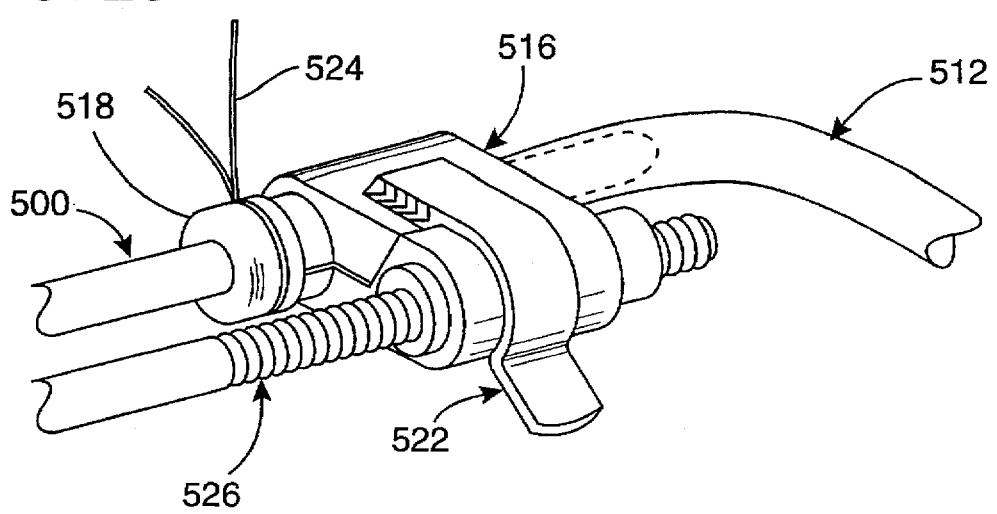

Referring now to FIG. 25, driver rod 526 is slid into bore 528 of handle 530 and then threadedly engaged with bore 532 of staple cartridge 516. FIG. 26 shows a close-up of staple cartridge 516 as it appears in its closed position.

Figure 27:
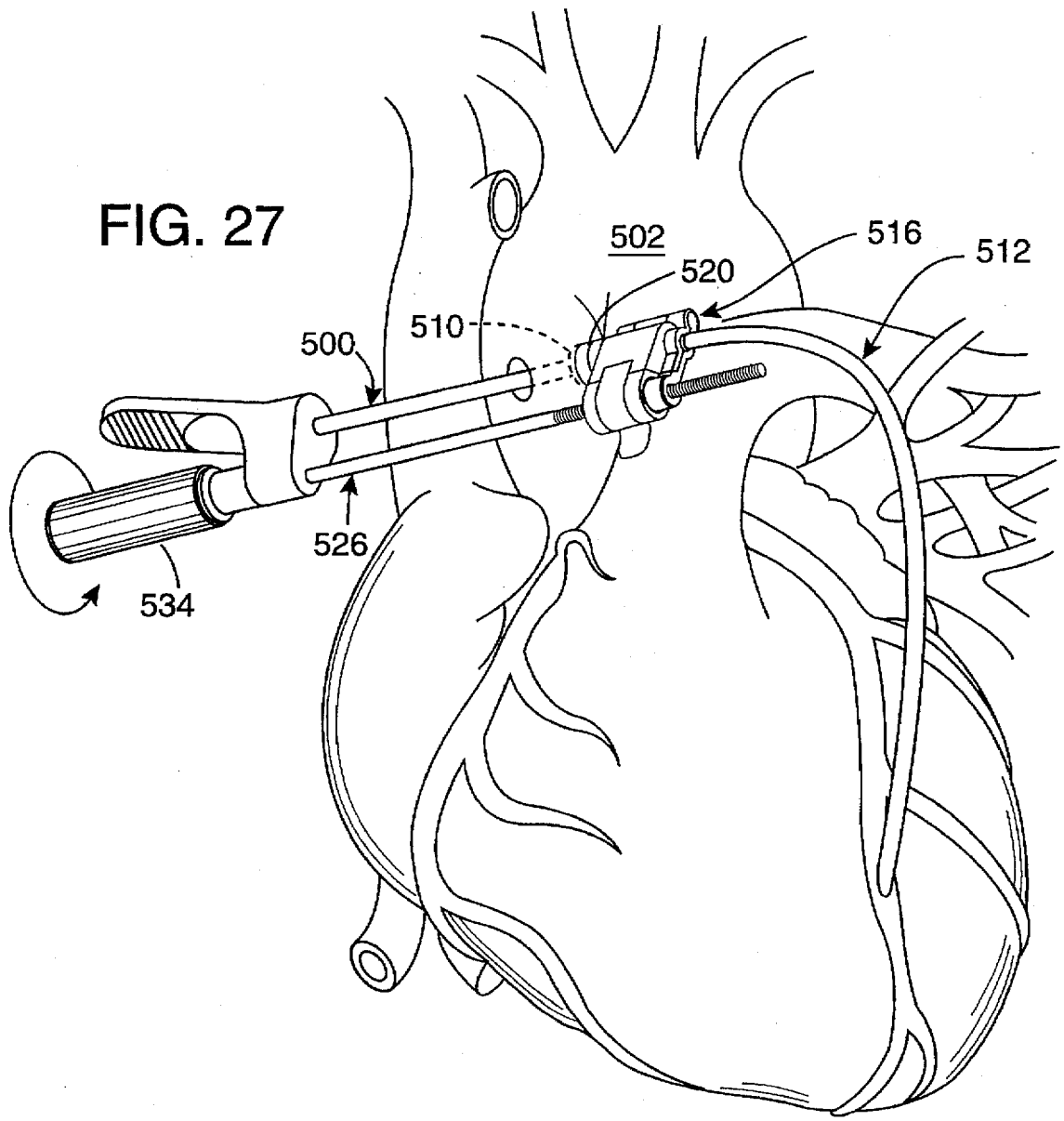
Figure 28:
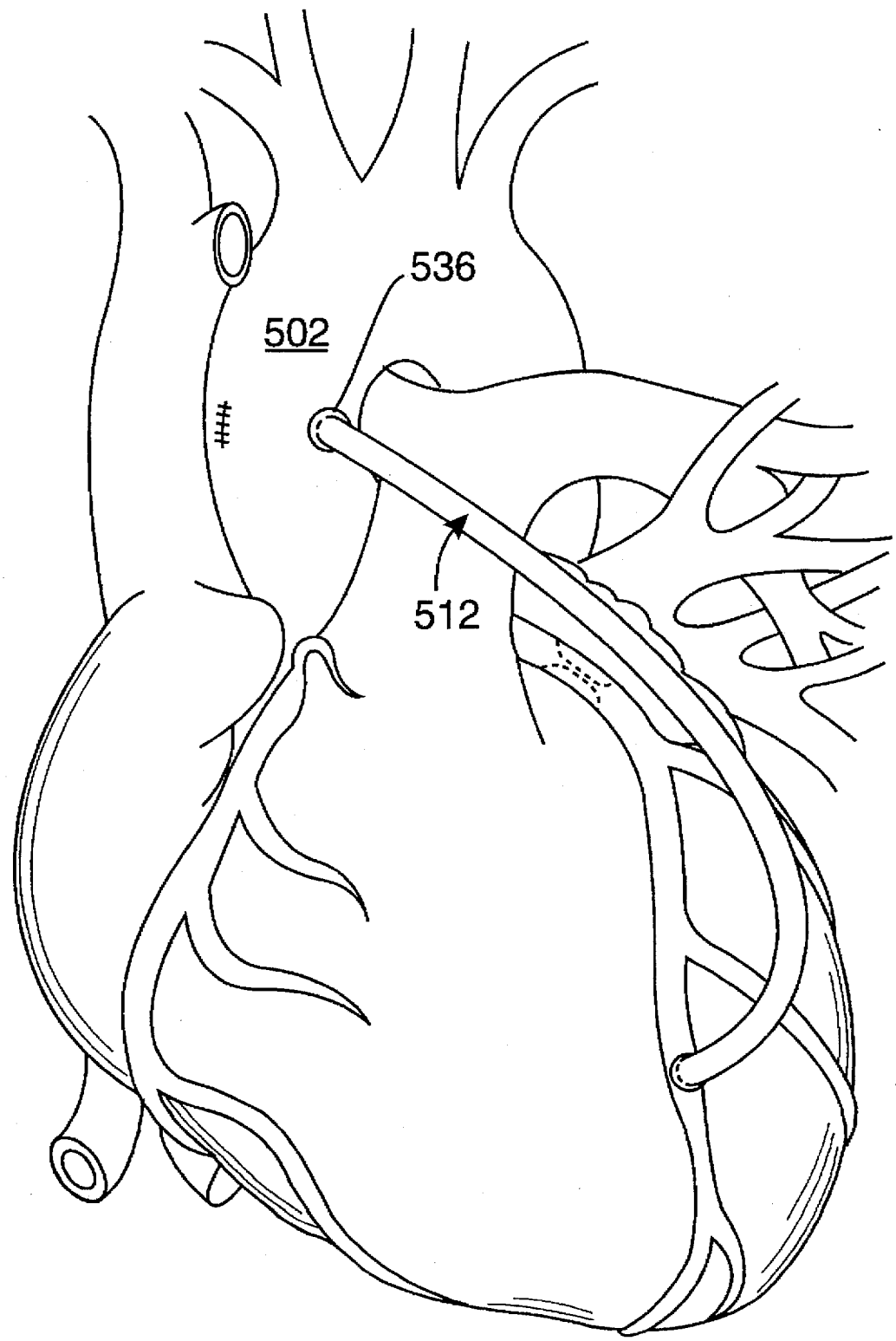

Moving now to FIG. 27, there is shown driver handle 534 rotated in a clockwise direction, bringing together anvil 510 and cylindrical sleeve 520. The clockwise rotation is continued until the aorta wall 502 is engaged with the distal end 518 of vein 512 upon which the staple driver pins (not visible) are fully engaged within each of the corresponding staple shafts (not visible), driving the staples (not visible) through the engaged tissue to create anastomotic bond 536 between aorta 502 and vein 512 (See FIG. 28).

It will be understood that the foregoing is only illustrative of the principles of the present invention, and that various modifications can be made by those skilled in the art without departing from the scope and spirit of the invention. For example, the particular stapler structural configurations shown are not critical and other configurations can be used if desired. One possible alternative for the configuration illustrated in FIG. 17 is to have a vessel rod that is retractable (e.g., by means of a telescoping rod). In addition, the vessel rod of this alternative embodiment can be curved to facilitate the anastomotic procedure if necessary. Also, the structure and method of the present invention can be employed thoracoscopically.

Accordingly, it is intended that the appended claims will cover any such modifications or embodiments that fall within the scope of the invention.

What is claimed is:

1. A surgical stapling instrument for stapling a tubular tissue structure having at least one distal end to a luminal structure such as a vascular lumen or another tubular tissue structure, comprising:

a rod having a circumference sufficient to pass within the tubular tissue structure;

an anvil mounted on said rod, said anvil having an array of staple deforming means theron and having a size sufficient to pass through a surgically formed opening in and to be accommodated within the luminal structure;

a generally tubular staple cartridge containing a plurality of staples and having an inner passage sufficient to axially accommodate the tubular tissue structure between said rod and the inner surface of said staple cartridge and sufficient to be movable axially with respect to said rod, and having a staple delivery end having an outer dimension small enough so that the tubular tissue structure can be everted over said staple delivery end of said staple cartridge, said staple delivery end being positioned toward said array of staple deforming means;

means for clamping the everted portion of the tubular tissue structure and the luminal structure adjacent to the surgically formed opening between said staple cartridge and said anvil; and means for ejecting said plurality of staples through said everted portion of the tubular tissue structure and the luminal structure to engage said staple deforming means on said anvil to deform said staples and create a bond between the tubular tissue structure and the luminal structure.

2. The instrument of claim 1, wherein said means for clamping comprises means for variably positioning said tubular staple cartridge axially along said rod such that stapling is optimized.

3. The instrument of claim 1, wherein said means for ejecting comprises means for driving said plurality of staples through said staple cartridge.

4. A surgical stapling instrument for stapling a tubular tissue structure to a vascular lumen, comprising:

a rod having an anvil distally mounted on one end of said rod, said rod having a circumference sufficient to pass within the tubular tissue structure and said anvil having an array of staple deforming means theron and having a size sufficient to pass through a surgically formed opening in, and to be accommodated within the luminal structure;

a generally tubular staple cartridge containing a plurality of staples and having an inner passage sufficient to axially accommodate the tubular tissue structure between said rod and the inner surface of said staple cartridge and sufficient to be movable axially with respect to said rod, and having a staple delivery end having an array of staple delivery means and having an outer dimension small enough so that the tubular tissue structure can be everted over said staple deforming end of said staple cartridge, said staple delivery end being positioned toward said array of staple deforming means;

means for clamping the everted portion of the tubular tissue structure and the luminal structure adjacent said surgically formed opening between said staple cartridge and said anvil; and means for ejecting said plurality of staples from said staple delivery means and through said everted portion of the tubular tissue structure and the luminal structure to engage said staple deforming means on said anvil to deform said staples and create a bond between the tubular tissue structure and the lirnininal structure.

5. The instrument of claim 4 wherein said array of staple deforming means and said array of staple delivery means are tear drop shape.

6. A surgical stapling instrument for stapling a tubular tissue structure to a vascular lumen, comprising:

a rod having an anvil centrally mounted to said rod, said rod having a circumference sufficient to pass within the tubular tissue structure, and said anvil having an array of staple deforming means theron and having a size sufficient to pass through a surgically formed opening in the luminal structure;

a generally tubular staple cartridge containing a plurality of staples and having an inner passage sufficient to axially accommodate the tubular tissue structure between said rod and the inner surface of said staple cartridge and sufficient to be movable axially with respect to said rod, and having a staple delivery end having an array of staple delivery means and having an outer dimension small enough so that the tubular tissue structure can be everted over said staple delivery end of said staple cartridge, said staple delivery end being positioned toward said array of staple deforming means;

means for clamping said everted portion of the tubular tissue structure and the luminal structure adjacent said surgically formed opening between said staple cartridge and said anvil; and means for ejecting said plurality of staples through said everted portion of the tubular tissue structure and the luminal structure to engage said staple deforming means on said anvil to deform said staples and create a bond between the tubular tissue structure and the lumininal structure.

7. The instrument of claim 6, wherein said rod is retractable along its axis.

8. The instrument of claim 6, wherein said array of staple deforming means and said array of staple delivery means are circular.

9. A method for stapling a tubular tissue structure to a luminal structure, comprising the steps of:

inserting a rod having an anvil into the tubular tissue structure;

securing the tubular structure to said rod;

inserting said rod into a tubular staple cartridge;

everting the end of the tubular tissue structure proximate to said anvil over said tubular staple cartridge;

securing said end of the tubular tissue structure proximate to said anvil to said tubular staple cartridge;

positioning said anvil in the luminal structure via a surgically formed opening in therein;

moving said tubular staple cartridge along said rod toward said head until the tubular structure and the luminal structure are engaged;

clamping the everted portion of the tubular tissue structure and the luminal structure adjacent said surgically formed opening between said tubular staple cartridge and said anvil; and ejecting a plurality of staples from said tubular staple cartridge through said everted portion of the tubular tissue structure and the luminal structure to engage said anvil to deform said staples and create a bond between the tubular tissue structure and the luminal structure.

10. A method for stapling a tubular tissue structure to a luminal structure, comprising the steps of:

inserting a rod having a centrally mounted anvil into the luminal structure via a surgically formed opening therein such that said rod transects opposing walls of the luminal structure and such that said anvil is positioned within the luminal structure;

inserting one end of said rod into the tubular tissue structure;

positioning the portion of said rod accommodating the tubular tissue structure and the accommodated end of the tubular tissue structure in a tubular staple cartridge;

everting said accommodated end of the tubular tissue structure over said tubular staple cartridge;

securing the everted end of the tubular tissue structure to said tubular staple cartridge;

moving said tubular staple cartridge axially with respect to said rod toward said anvil until the tubular structure and the luminal structure are engaged;

clamping said everted end of the tubular tissue structure and the luminal structure adjacent said surgically formed opening between said tubular staple cartridge and said anvil; and ejecting a plurality of staples from said tubular staple cartridge through said everted portion of the tubular tissue structure and the luminal structure to engage said anvil to deform said staples and create a bond between the tubular tissue structure and the limininal structure.

11. A surgical stapling instrument for stapling a tubular tissue structure having at least one distal end to a luminal structure such as a vascular lumen or another tubular tissue structure, comprising:

a rod having a circumference sufficient to pass within the tubular tissue structure;

an anvil coupled to said rod and configured to be positioned through a surgically formed opening in and to be accommodated within luminal structure;

a staple cartridge containing a plurality of staples and having an inner surface defining an inner passage extending from a proximal end to a distal end thereof, said passage being sufficiently dimensioned to axially accommodate the tubular tissue structure between said rod and the inner surface from the proximal end to the distal end of said staple cartridge, and having an outer dimension small enough so that an everted portion of the tubular tissue structure to be everted over the distal end of said staple cartridge;

at least one driver pin moveable relative to said staple cartridge for ejecting said plurality of staples through the everted portion of the tubular tissue structure and the luminal structure to engage said anvil to deform said staples and create a bond between the tubular tissue structure and the luminal structure; and a clamping mechanism which clamps the everted portion and the luminal structure adjacent to the surgically formed opening between the staple cartridge and the anvil.

12. The instrument of claim 11, wherein said staple cartridge comprises an array of staple delivery shafts.

13. The instrument of claim 12, wherein said at least one driver pin comprises an array of pins adapted to be accommodated within said array of staple delivery shafts and means for driving said array of pins through said array of staple delivery shafts such that said plurality of staples is ejected therefrom.

14. The instrument of claim 13, wherein said anvil comprises an array of staple deforming means thereon, said array of staple deforming means being axially aligned with said array of staple delivery shafts.

15. The instrument of claim 12, wherein said staple delivery shafts are disposed in a non-circular arrangement.

16. The instrument of claim 15 wherein said staple deforming means are disposed in a non-circular arrangement.

17. The instrument of claim 16 wherein said non-circular arrangement is tear-drop shape.

18. A method for stapling a tubular tissue structure to a luminal structure, comprising the steps of:

inserting a rod having a distally mounted anvil into the tubular tissue structure;

inserting said rod and an end of said tubular tissue structure into a staple cartridge;

everting the end of the tubular tissue structure proximate to said anvil over said staple cartridge;

positioning said anvil in the luminal structure via a surgically formed opening in therein; and ejecting a plurality of staples from said tubular staple cartridge through the everted end of the tubular tissue structure and the luminal structure to engage said anvil to deform said staples and create a bond between the tubular tissue structure and the luminal structure.

19. The method of claim 18 wherein said bond created between the tubular tissue structure and the luminal structure is non-circular.

20. The method of claim 19 wherein said bond has a tear drop shape.

21. A method for stapling a tubular tissue structure to a luminal structure, comprising the steps of:

inserting a rod having a centrally mounted anvil into the luminal structure via a surgically formed opening therein such that said rod transects opposing walls of the luminal structure and such that said anvil is positioned within the luminal structure;

inserting one end of said rod into the tubular tissue structure;

positioning the portion of said rod accommodating the tubular tissue structure and the accommodated end of the tubular tissue structure in a staple cartridge;

everting said accommodated end of the tubular tissue structure over said staple cartridge; and ejecting a plurality of staples from said staple cartridge through said everted portion of the tubular tissue structure and the luminal structure to engage said anvil to deform said staples and create a bond between the tubular tissue structure and the luminal structure.

22. The method of claim 21 wherein said bond created between the tubular tissue structure and the luminal structure is non-circular.

23. A surgical stapling instrument for stapling a tubular tissue structure having at least one distal end to a luminal structure such as a vascular lumen or another tubular tissue structure, comprising:

an elongated rod having a transverse cross-sectional dimension sufficient to pass within the tubular tissue structure;

an anvil coupled to said rod and configured to be positioned through a surgically formed opening in and to be accommodated within luminal structure;

a staple cartridge containing a plurality of staples and having an inner surface defining an inner passage extending from a proximal end to a distal end thereof, said passage being sufficiently dimensioned to axially accommodate the tubular tissue structure between said rod and the inner surface from the proximal end to the distal end of said staple cartridge, said staple cartridge further having an outer dimension sufficiently small to enable an everted portion of the tubular tissue structure to be everted over the distal end of said staple cartridge; and at least one driver pin moveable relative to said staple cartridge for ejecting said plurality of staples through the everted portion of the tubular tissue structure and the luminal structure to engage said anvil to deform said staples and create a bond between the tubular tissue structure and the luminal structure.

24. The stapling instrument of claim 23 further including:

a securing device which removably secures the everted portion of the tubular tissue structure to the staple cartridge.

25. The stapling instrument of claim 24 wherein, the securing device includes a string formed to secure the everted portion against an outer surface of the staple cartridge.

26. The stapling instrument of claim 25 wherein, the securing device further includes a groove defined by the outer surface of the staple cartridge which cooperates with the string to secure the everted portion to the staple cartridge.

27. The stapling instrument of claim 23 wherein, the distal end of the staple cartridge is tapered inwardly.

28. The stapling instrument of claim 23 further including:

a retaining device which removably retains a proximal end of the tubular tissue structure to the rod.

29. The stapling instrument of claim 28 wherein, the retaining device includes a string formed to secure the proximal end of the tubular tissue structure against an outer surface of the rod.

30. The stapling instrument of claim 29 wherein, the retaining device further includes a groove defined by the outer surface of the rod which cooperates with the string to retain the tubular tissue structure to the rod.

31. The stapling instrument of claim 23 wherein, the staple cartridge and the anvil cooperate with the driver pin to dispose the plurality of staples in a non-circular arrangement.

32. An end-to-side surgical stapling instrument for stapling a tubular tissue structure having at least one distal end to a side of a luminal structure such as a vascular lumen or another tubular tissue structure, comprising:

an elongated rod having a transverse cross-sectional dimension sufficient to pass within the tubular tissue structure;

a disk-shaped anvil coupled to a distal end of said rod and having relatively low side profile extending from a proximal end to a distal end thereof, and configured to be positioned through a surgically formed opening in the side of and to be accommodated within luminal structure;

a staple cartridge containing a plurality of staples and having an inner surface defining an inner passage sufficient to axially accommodate the tubular tissue structure between said rod and the inner surface, and having an outer dimension sufficiently small to enable an everted portion of the tubular tissue structure to be everted over the distal end of said staple cartridge; and at least one driver pin moveable relative to said staple cartridge for ejecting said plurality of staples through the everted portion of the tubular tissue structure and the luminal structure to engage said anvil to deform said staples and create a bond between the tubular tissue structure and the side of the luminal structure.

33. The stapling instrument of claim 32 wherein, an outer edge of the anvil is beveled.

34. The stapling instrument of claim 32 wherein, the disk-shaped anvil is circular.

35. The stapling instrument of claim 32 wherein, the disk-shaped anvil is tear-drop shaped.

36. The stapling instrument of claim 32 further including:

a securing device which removably secures the everted portion of the tubular tissue structure to the staple cartridge.

37. The stapling instrument of claim 32 wherein, the staple cartridge and the anvil cooperate with the driver pin to dispose the plurality of staples in a non-circular arrangement.

38. A surgical stapling instrument for stapling a tubular tissue structure having at least one distal end to a luminal structure such as a vascular lumen or another tubular tissue structure, comprising:

an elongated rod having a transverse cross-sectional dimension sufficient to pass within the tubular tissue structure;

an anvil coupled to said rod and configured to be positioned through a surgically formed opening in and to be accommodated within luminal structure;

an elongated housing defining a bore formed and dimensioned for sliding receipt of the rod therein;

a disposable staple cartridge formed to removable couple to said housing and containing a plurality of predisposed staples therein, said staple cartridge having an inner surface defining an inner passage sufficiently dimensioned to axially accommodate the tubular tissue structure between said rod and the inner surface, and further having an outer dimension sufficiently small to enable an everted portion of the tubular tissue structure to be everted over the distal end of said staple cartridge; and at least one driver pin movable relative to said staple cartridge for ejecting said plurality of staples through the everted portion of the tubular tissue structure and the luminal structure to engage said anvil to deform said staples and create an anastomotic bond between the tubular tissue structure and the luminal structure.

39. The stapling instrument of claim 38 wherein, said one driver pin comprises an array of pins fixedly mounted to and extending outward from a face wall at the distal end of the housing, and said staple cartridge defining an array of staple delivery shafts each having a staple predisposed therein, and each shaft further configured to slidingly accommodate one driver pin of the array of pins therein in a direction toward the staple and the anvil to eject the staple from the cartridge.

40. The stapling instrument of claim 39 further including:

a clamping mechanism which selectively urges the anvil and the array of pins toward one another to enable ejection of the array of staples from the cartridge.

41. The stapling instrument of claim 40 wherein, said array of pins are disposed around the bore.

42. The stapling instrument of claim 40 wherein, said anvil includes an array of staple deforming slots therein positioned in axial alignment with the array of staple delivery pins.

43. The stapling instrument of claim 42 further including:

an alignment device operatively engaged between the pins and the anvil to align the array of pins with the corresponding deforming slots in the anvil.

\* \* \* \* \*